United States Patent [19]
Ishibashi

[11] Patent Number: 5,322,610
[45] Date of Patent: Jun. 21, 1994

[54] AUTOMATIC ION CONCENTRATION ANALYZING APPARATUS

[75] Inventor: Kiyochica Ishibashi, Tama, Japan
[73] Assignee: Olympus Optical Co., Ltd., Tokyo, Japan
[21] Appl. No.: 776,770
[22] Filed: Oct. 18, 1991

[30] Foreign Application Priority Data

Oct. 19, 1990 [JP] Japan .............................. 2-108937[U]

[51] Int. Cl.$^5$ ........................................... G01N 27/26
[52] U.S. Cl. ................................... 204/409; 204/416; 204/435; 422/82.03
[58] Field of Search ............... 204/407, 409, 416, 435; 422/82.03

[56] References Cited

U.S. PATENT DOCUMENTS 5,017,339  5/1991  Marsoner et al. .................... 204/409
5,046,496  9/1991  Betts et al. ........................... 204/409

Primary Examiner—John Niebling
Assistant Examiner—Bruce F. Bell
Attorney, Agent, or Firm—Stevens, Davis, Miller & Mosher

[57] ABSTRACT

An automatic ion concentration analyzing apparatus including a plurality of ion concentration measuring cells each having an ion selective electrode and a reference electrode; a single pair of sample suction nozzle and nozzle driving device for picking up the sample to be measured; a sample supplying device for selectively supplying the sample sucked in the nozzle to the ion concentration measuring cells; and calculation and display section, which is commonly used for calculating the ion concentration concerning samples to be measured by comparing the measurement results of electric potentials induced on the ion selective electrode and the reference electrode. In the apparatus according to the invention, although the apparatus can be made small in size, the ion concentration of the samples to be measured can be analyzed in an effective manner.

5 Claims, 4 Drawing Sheets

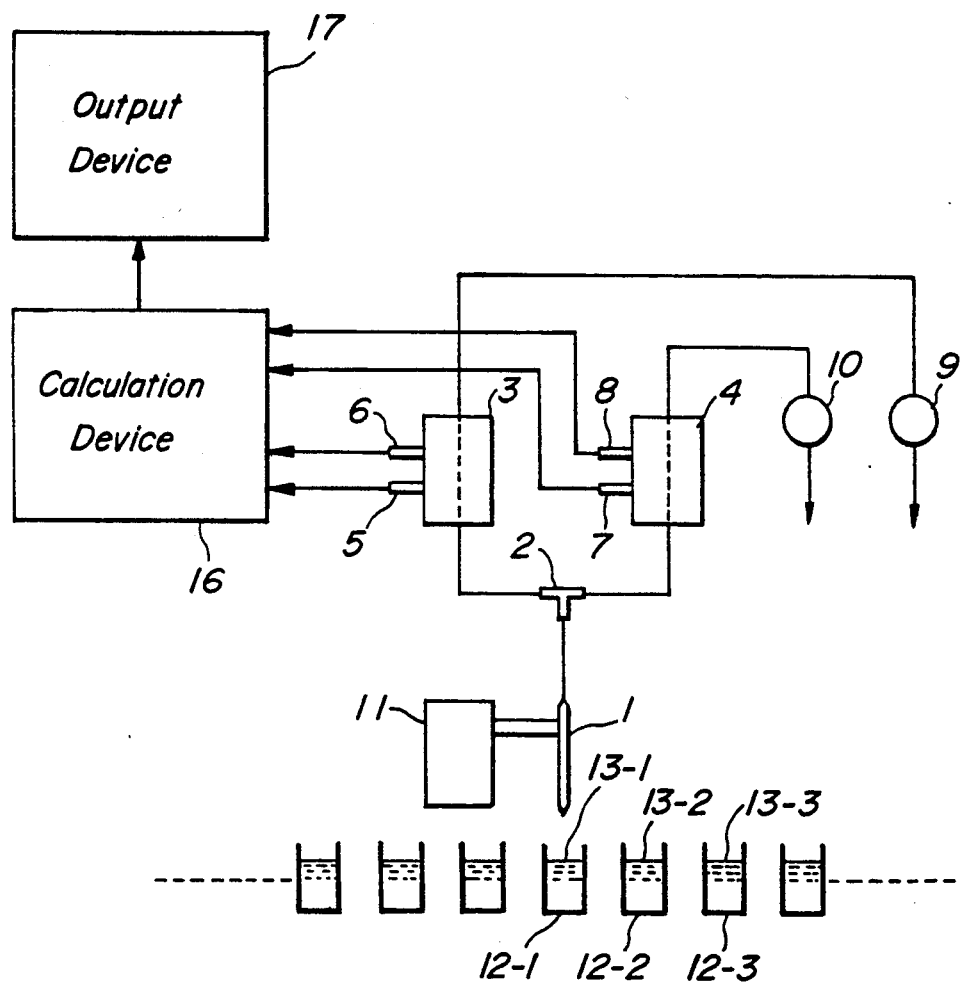
FIG_1

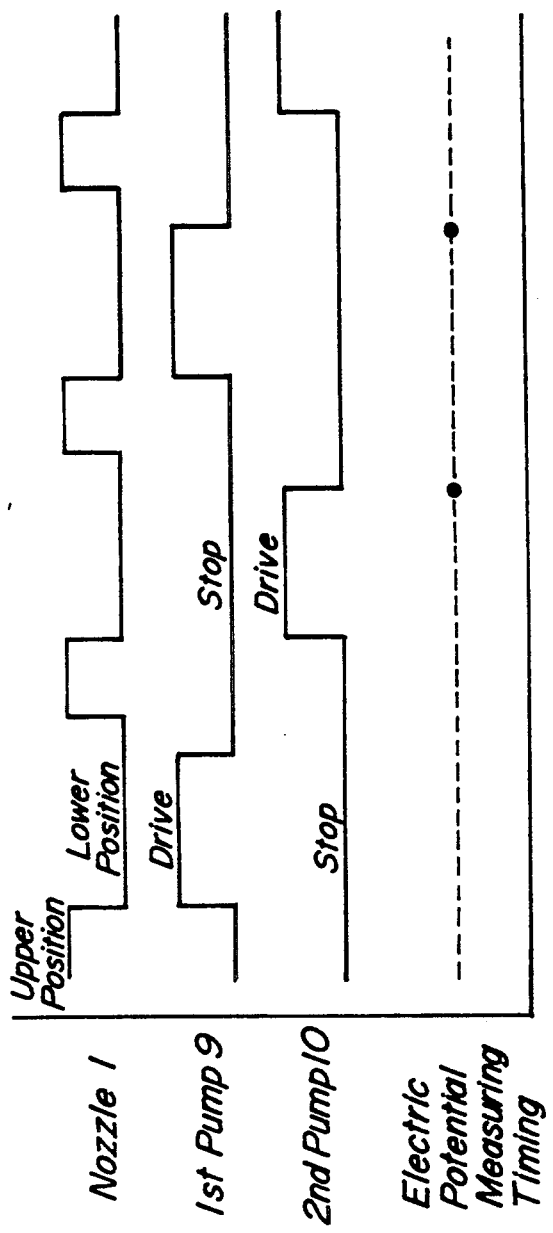

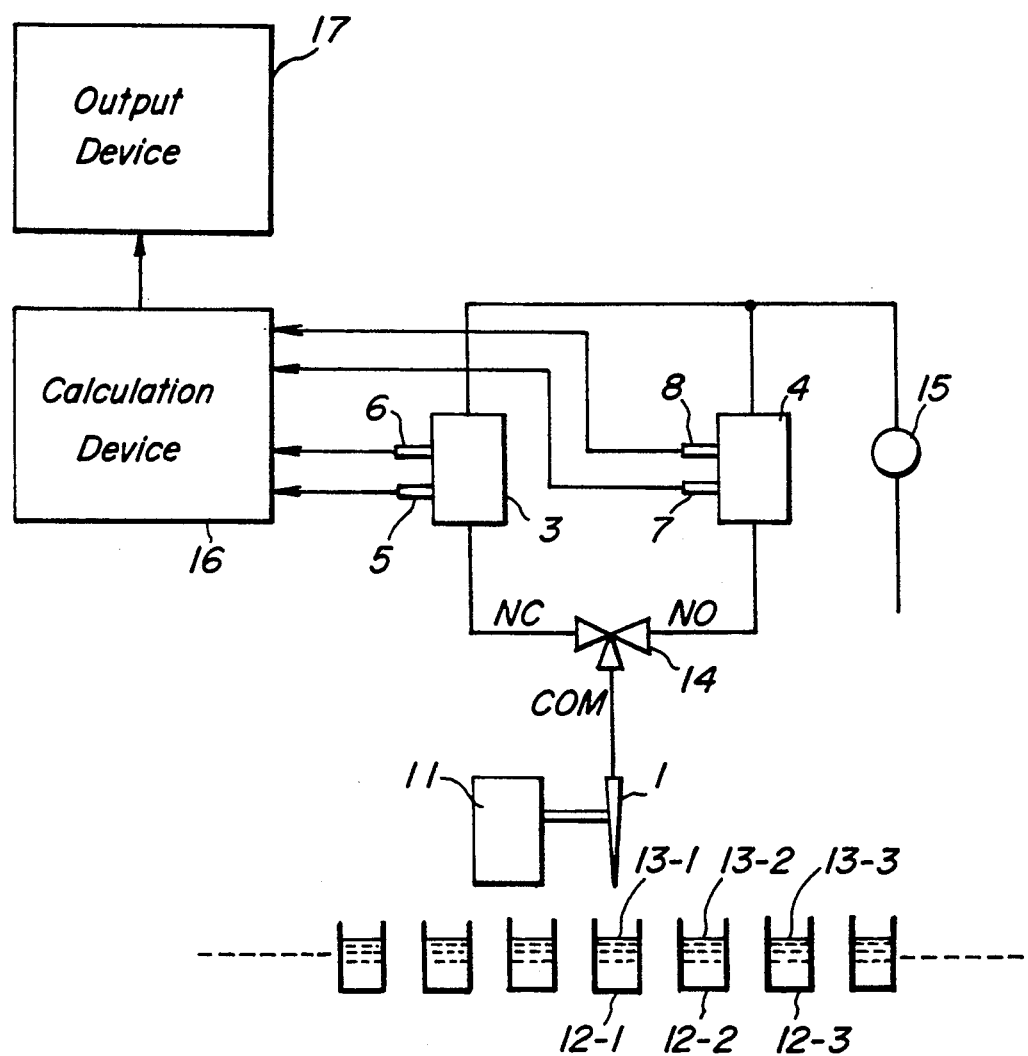
FIG_3

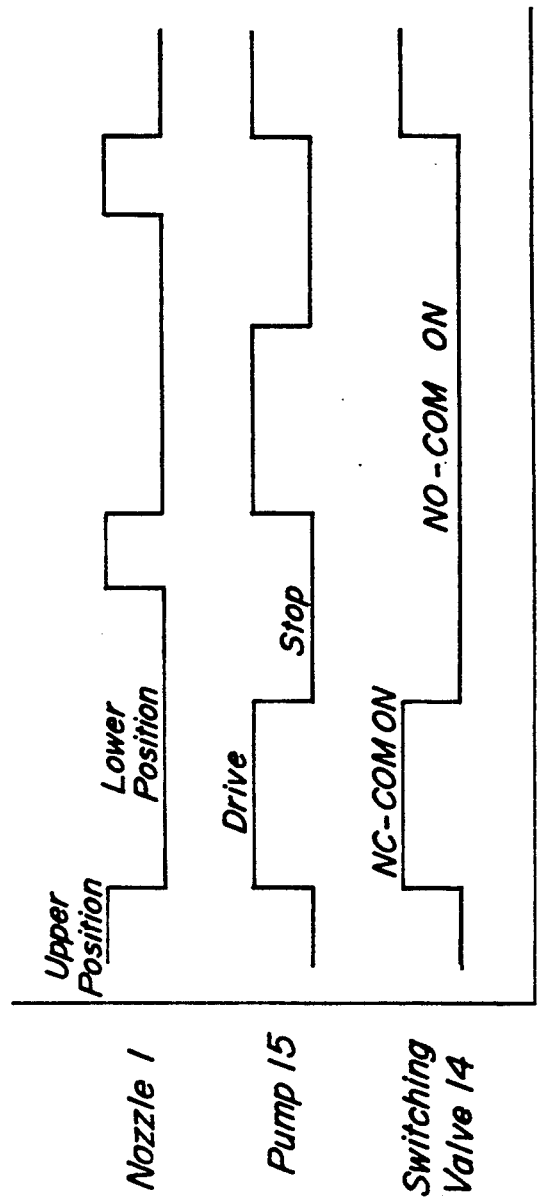

AUTOMATIC ION CONCENTRATION ANALYZING APPARATUS

BACKGROUND OF THE INVENTION

1. Field of the Invention

The present invention relates to an automatic ion concentration analyzing apparatus for use in quantitative analysis of ion concentration in a sample liquid such as blood and urea. In the apparatus according to the invention, the quantitative analysis of ion concentration is performed with the aid of ion selective electrodes.

2. Description of the Related Art

In a conventional automatic ion concentration analyzing apparatus using ion selective electrodes as an ion concentration measuring element, a single ion selective electrode is used for measuring a concentration of a single kind of ion included in the sample. But, this apparatus has a drawback that an analyzing speed cannot be made fast due to the responding speed of the ion selective electrode. In order to increase the analyzing speed of the ion concentration, an improvement of the apparatus is suggested, in which a plurality of ion selective electrodes are used for measuring the concentration of a single kind of ion included in the sample to be measured. However, since a number of ion concentration measuring systems are required in the improvement of the apparatus, the size of the analyzing apparatus as a whole becomes great.

In Japanese Utility Model Publication No. 62-8523, such an ion concentration analyzing apparatus is disclosed that a plurality of ion concentration measuring cells each comprising an ion selective electrode are provided, but a calculating section for calculating the measuring results measured in the ion concentration measuring cells and a displaying section for displaying the measuring results are commonly used for the plurality of ion concentration measuring systems. That is to say, electric signals supplied from the plurality of ion concentration measuring cells are commonly processed in the commonly used calculating and displaying sections. In the apparatus disclosed in this Japanese Utility Model Publication, although a plurality of ion selective electrodes are used for measuring the concentration of the single kind of ion included in the sample to be measured, it is attempted to make the apparatus as a whole, small in size. However, in the ion concentration analyzing apparatus, the ion concentration measuring section occupies a large capacity and the mechanism is rather more complex than the calculating and displaying sections. That is to say, in the ion concentration measuring section of the apparatus, there are provided not only a plurality of sample suction nozzles but also a plurality of nozzle driving systems for moving the plurality of sample suction nozzles to sample pick up positions, where sample cups each containing a sample to be measured are fed to, and to a nozzle washing section. Further, it is necessary to provide a plurality of sample cup feeding systems for feeding the sample cups to the sample pick up positions. Therefore, the ion concentration analyzing apparatus using a plurality of ion selective electrodes could not help being large in size.

SUMMARY OF THE INVENTION

The present invention has for its object to provide an automatic ion concentration analyzing apparatus in which ion concentrations of samples can be effectively analyzed by using a plurality of ion selective electrodes, which is for a single kind of ion, the apparatus as a whole not becoming to be too large in size.

The automatic ion concentration analyzing apparatus according to the invention comprises:

a plurality of ion concentration measuring cells for measuring a concentration of one kind of ion included in a sample each comprising an ion selective electrode and a reference electrode;

a single sample suction nozzle for suctioning a sample being commonly used to supply said sample to said plurality of ion concentration measuring cells;

a sample supply means for selectively supplying the sample sucked in said sample suction nozzle to said plurality of ion concentration measuring cells;

a nozzle driving means for driving said sample suction nozzle so as to pick up said sample;

a calculating means for calculating an ion concentration of said sample by detecting electric potentials of said ion selective electrode and said reference electrode; and an output means for outputting a measurement result of said ion concentration of said sample.

BRIEF DESCRIPTION OF THE DRAWINGS

FIG. 1 is a schematic view showing a construction of an automatic ion concentration analyzing apparatus according to the first embodiment of the present invention;

FIG. 2 is a schematic view depicting a time chart of a movement of a nozzle transferring device, a first pump and a second pump, and electric potential measuring timing, at which the ion concentrations of samples are measured in the measuring cells;

FIG. 3 is a schematic view illustrating a construction of an automatic ion concentration analyzing apparatus according to the second embodiment of the present invention; and FIG. 4 is a schematic view representing a time chart of a movement of a nozzle transferring device, a pump and a switching valve provided in the apparatus according to the second embodiment.

DESCRIPTION OF THE PREFERRED EMBODIMENTS

FIG. 1 is a schematic view showing a construction of the automatic ion concentration analyzing apparatus according to the first embodiment of the present invention.

Sample vessels 12 each containing a sample 13 to be analyzed are successively fed to a sample pick up position by a sample vessel feeding device (not shown); at the sample pick up position the sample 13 is picked up by a suction nozzle 1. The nozzle 1 is driven by a nozzle driving device 11 in upper and lower directions to pick up the sample 13 contained in the sample vessels 12. The nozzle 1 is connected to a first measuring cell 3 and a second measuring cell 4, respectively, via a divergence tube 2. In the first and second measuring cells 3 and 4, there are provided ion selective electrodes 5, 7 and reference electrodes 6, 8, respectively. It should be noted that the ion selective electrodes 5 and 7 are the same type electrodes. The first measuring cell 3 is further connected to a first pump 9; and the sample 13 contained in the sample vessel 12 is supplied to the first measuring cell 3 by driving of the first pump 9. The second measuring cell 4 is also connected to a second pump 10; and the sample 13 is supplied to the second measuring cell 4 by driving of the second pump 10. In accordance to a concentration of ion included in the sample 13, which has been supplied to the first measuring box 3, an electric potential is induced on the ion selective electrode 5 and the reference electrode 6. Both electrodes 5 and 7 are connected to a calculating device 16, in which an electric potential difference between the ion selective electrode 5 and the reference electrode 6 measured in the first measuring cell 3 is calculated. The calculating device 16 is further connected to an output device, by which the calculated result is displayed on a monitor screen and may be printed out. In the same manner, the ion concentration of the sample 13 supplied to the second measuring cell 4 is also detected and outputted in the calculator 16 and the output device 17, which are commonly used for the first and second measuring cells 3 and 4. The sample 13 left in the nozzle 1 and the divergence tube 2 may be washed away with the aid of the sample to be measured next. The other known washing method can be applied therefor. If not only the inner wall of the nozzle 1 but also the outer wall thereof is necessary to be cleared, it may be possible to arrange to wipe the outer wall of the nozzle with a cloth or to clear it with the aid of air.

A series of ion concentration measuring operations performed in the apparatus according to the first embodiment will be explained below, referring the time chart shown in FIG. 2.

A nozzle 1 positioned at an upper position is lifted down to a lower position by the nozzle driving device 11 so as to suck a first sample 13-1 contained in a first sample vessel 12-1. Then, the first sample 13-1 sucked into the nozzle 1 is supplied to the first measuring cell 3 by driving of the first pump 9. After supplying the sample 13-1 into the first measuring cell 3, the first pump 9 is stopped to wait until the electric potentials are induced on the ion selective electrode 5 and the reference electrode 6 in response to the ion contained in the first sample 13-1. During this action, the nozzle driving device 11 works to lift up the nozzle 1 and then the second sample vessel 12-2 containing the second sample 13-2 is fed to the sample pick up position under the nozzle 1. Then the nozzle 1 is driven to be lifted down by the nozzle driving device 11; and thereafter the second pump 10 is driven such that the nozzle 1 sucks the second sample 13-2 and supplies the second sample 13-2 into the second measuring cell 4. After supplying the second sample 13-2 to the second measuring cell 4, the second pump 10 is stopped to wait for the reaction of the ion selective electrode 7 and the reference electrode 8 provided in the second measuring cell 4. On the other hand, in the first measuring cell 3, the electric potentials induced on the first ion selective electrode 5 and the reference electrode 6 are measured. The signal representing the electric potential measured in the first cell 3 is supplied to the calculator 16, in which the electric potential difference between the first ion selective electrode 5 and the reference electrode 6 is calculated. Next, a third sample 13-3 is supplied to the first measuring cell 3 in the same manner; and during the action the electric potentials induced on the second ion selective electrode 7 and the reference electrode 8 in accordance with the ion concentration of the second sample 13-2 are measured in the second measuring cell 4. In such manner, the samples 13 fed to the sample pick up position under the nozzle 1 are alternately supplied to the first and second measuring cells 3 and 4 to be analyzed.

FIG. 3 is a schematic view illustrating a construction of the second embodiment of the apparatus according to the present invention. It should be noted that the same numerical numbers are denoted on the same elements used in the first embodiment explained in the above.

In the second embodiment, there is provided a switching valve 14 instead of the divergence tube 2 and only one pump 15 is connected to the first and second measuring cells 3 and 4. The sample suction nozzle 1 is connected to a common port COM of the switching valve 14. A normal closed port NCP of the switching vale 14 is connected to the first measuring cell 3; and a normal open port NOP to the second measuring cell 4. The first and second measuring cells 3 and 4 are connected to the commonly used pump 15; and when the pump 15 is operated under the condition that the normal closed port NCP and the common port COM of the switching valve 14 are made ON, the sample 13 is supplied to the first measuring cell 3; and when the pump 15 is operated under the condition that the normal open port and the common port of the switching valve 14 are made ON, the sample 13 is supplied to the second measuring cell 4. Since the other construction of the apparatus is the same as that of the first embodiment, a repetitive explanation therefor is omitted.

The operational movements of the sample suction nozzle 1, the pump 15 and the switching valve 14 will be explained below, referring the time chart shown in FIG. 4. When the nozzle 1 is lifted down in the lower direction at the sample pick up position by driving the nozzle driving device 11, the pump 15 is driven such that the nozzle 1 sucks the sample 13-1 contained in the sample vessel 12-1. Thereafter, the connection between the normal closed port NCP and the common port COP of the switching valve 14 is made ON. After the sample 13-1 is supplied into the first measuring cell 3 by driving the commonly used pump 15, the connection of the switching valve 14 is switched to the condition that the connection of the normal open port NOP and the common port COP is made ON. And then the nozzle 1 is lifted up, and the next sample cap 12-2 is fed to the sample pick up position under the nozzle 1. Then the nozzle 1 is lifted down to suck the sample 13-2; the pump 15 is driven to supply the sample 13-2 into the second measuring cell 4. After the supply of the sample 13-2 to the second measuring cell 4, the nozzle 1 is lifted up again and the connection of the valve 14 is switched again to the condition that the normal closed port NCP and the common port COM is made ON. In such a manner, the sample, which is fed to the sample pick up position successively, is alternately supplied to the measuring cells 3 and 4; and the ion concentration concerning each sample 13 is measured.

In the above mentioned embodiments, two ion concentration measuring systems are provided, however, it may be possible to provide an apparatus having three or more ion concentration measuring systems, in which the samples are supplied to the plurality of measuring cells and the ion concentration concerning the respective samples are measured in a successive manner. Further, it may be possible to arrange a plurality of different kinds of ion selective electrodes in each measuring cell in order to measure the concentrations of a plurality of different kinds of ion included in the sample. Furthermore, a sample whose ion concentration is unknown, a diluted sample whose ion concentration is unknown, and a sample, whose ion concentration is known, used for a correction purpose may be measured in the apparatus according to the invention.

As explained in the above, according to the present invention, a plurality of measuring cells are provided, but only a pair of sample suction nozzle and nozzle driving device is required. Further, although only the sample cap feeder for one ion concentration measuring system is required in the apparatus, the ion concentration of the sample can be analyzed in an effective manner.

What is claimed is:

1. A reusable automatic ion concentration analyzing apparatus comprising:
    a plurality of ion concentration measuring cells which measures a concentration of at least one kind of ion included in a sample, each of said measuring cells comprising at least one ion selective electrode and a reference electrode, all of said ion selective electrodes being of the same kind;
    a single sample suction nozzle, which suctions a sample, being commonly used to supply said sample to said plurality of ion concentration measuring cells;
    a sample supply means which selectively supplies the sample sucked in said sample suction nozzle to a selected one of said plurality of ion concentration measuring cells, said selected one ion concentration cell not containing a sample whose ion concentration has just been measured;
    a nozzle driving means which drives said sample suction nozzle so as to pick up said sample in a sample vessel at a sample pick up position, a plurality sample vessels transportable successively through said position;
    a calculating means which calculates an ion concentration of said sample by detecting electric potentials between said ion selective electrode and said reference electrode; and
    an output means which outputs a measurement result of said ion concentration of said sample.

2. The automatic ion concentration analyzing apparatus according to claim 1, wherein:
    said sample supply means comprises a divergence tube which connects said sample suction nozzle and said plurality of ion concentration measuring cells, and a plurality of pumps, corresponding to said plurality of ion concentration measuring cells, respectively, which performs the suction of the nozzle.

3. The automatic ion concentration analyzing apparatus according to claim 2, wherein:
    said divergence tube connects said sample suction nozzle said first and second ion concentration measuring cells and said first and second ion concentration measuring cells are connected to first and second pump; and
    ion concentrations of the samples successively supplied to the first and second ion concentration measuring cells are alternately measured in the first and second measuring cells by driving said first and second pumps alternately.

4. The automatic ion concentration analyzing apparatus according to claim 1, wherein:
    said sample supply means comprises a switching valve which connects said sample suction nozzle and said plurality of ion concentration measuring cells, and a single pump which performs the suction of the nozzle in accordance with a measuring condition in said plurality of ion concentration measuring cells.

5. The automatic ion concentration analyzing apparatus according to claim 4, wherein:
    said switching valve comprises a common port, a normal closed port and a normal open port; said common port is connected to said sample suction nozzle and the normal closed port is connected to a first ion concentration measuring cell and the normal open port is connected to a second ion concentration measuring cell; and
    ion concentrations of the samples successively supplied to the first and second measuring cells are alternately measured by switching said switching valve and driving said single pump.

* * * * *